(12) United States Patent
Schall et al.

(10) Patent No.: US 11,020,167 B2
(45) Date of Patent: Jun. 1, 2021

(54) SYSTEM FOR SIMULTANEOUS TISSUE COAGULATION AND TISSUE DISSECTION

(71) Applicant: Erbe Elektromedizin GmbH, Tuebingen (DE)

(72) Inventors: Heiko Schall, Nuertingen (DE); Achim Brodbeck, Metzingen (DE); Rolf Weiler, Kusterdingen (DE); Volker Mayer, Tuebingen (DE); Tobias Amann, Geislingen (DE)

(73) Assignee: Erbe Elektromedizin GmbH, Tuebingen (DE)

( * ) Notice: Subject to any disclaimer, the term of this patent is extended or adjusted under 35 U.S.C. 154(b) by 1007 days.

(21) Appl. No.: 14/844,799

(22) Filed: Sep. 3, 2015

(65) Prior Publication Data

US 2016/0066980 A1 Mar. 10, 2016

(30) Foreign Application Priority Data

Sep. 8, 2014 (EP) .................................... 14183945

(51) Int. Cl.
*A61B 18/14* (2006.01)
*A61B 18/12* (2006.01)
(Continued)

(52) U.S. Cl.
CPC ...... *A61B 18/1442* (2013.01); *A61B 18/1206* (2013.01); *A61B 18/1445* (2013.01);
(Continued)

(58) Field of Classification Search
CPC ...... A61B 18/1445; A61B 2018/00601; A61B 2018/00607; A61B 2018/0063
See application file for complete search history.

(56) References Cited

U.S. PATENT DOCUMENTS 5,700,261 A * 12/1997 Brinkerhoff ....... A61B 18/1445
606/205
6,174,309 B1 * 1/2001 Wrublewski ....... A61B 18/1442
606/45
(Continued)

FOREIGN PATENT DOCUMENTS

CN 101677832 A 3/2010
CN 101969874 A 2/2011
(Continued)

OTHER PUBLICATIONS

Office action in corresponding Korean Application No. 2015-0122675, dated Nov. 15, 2017, 14 pages.
(Continued)

*Primary Examiner* — Linda C Dvorak
*Assistant Examiner* — Ryan T Clark
(74) *Attorney, Agent, or Firm* — Fitch, Even, Tabin & Flannery LLP (57) ABSTRACT

An instrument (10) provided for simultaneous coagulation and dissection of tissue has tissue receptacles between the cutting electrode and the sealing electrode for the formation of tissue bulges to secure the tissue in the tool during the sealing process. In order to make it possible to form voluminous tissue bulges and to prevent their atrophy, the cutting electrode is supplied by a current limiting component, preferably in the form of a coupling capacitor. Thereby, in particular, in tissue that can be cut through easily, but which requires a long time for sealing, a high degree of process safety is achieved.

17 Claims, 4 Drawing Sheets

(51) Int. Cl.
  *A61B 18/00* (2006.01)
  *A61B 18/16* (2006.01)
(52) U.S. Cl.
  CPC .............. *A61B 18/1482* (2013.01);
      *A61B 2018/00077* (2013.01); *A61B 2018/00083* (2013.01); *A61B 2018/00178* (2013.01); *A61B 2018/00607* (2013.01); *A61B 2018/1286* (2013.01); *A61B 2018/1467* (2013.01); *A61B 2018/162* (2013.01)

(56) References Cited

U.S. PATENT DOCUMENTS

| | | | |
|---|---|---|---|
| 7,803,156 B2 | 9/2010 | Eder et al. | |
| 8,394,094 B2 | 3/2013 | Edwards et al. | |
| 2003/0088245 A1* | 5/2003 | Woloszko | A61B 18/148 606/41 |
| 2003/0216733 A1 | 11/2003 | McClurken | |
| 2004/0049185 A1* | 3/2004 | Latterell | A61B 18/1442 606/48 |
| 2005/0113826 A1 | 5/2005 | Johnson et al. | |
| 2005/0124987 A1 | 6/2005 | Goble | |
| 2007/0185482 A1 | 8/2007 | Eder et al. | |
| 2007/0265616 A1 | 11/2007 | Couture et al. | |
| 2008/0015573 A1 | 1/2008 | Rossi | |
| 2008/0058802 A1 | 3/2008 | Couture et al. | |
| 2008/0082095 A1 | 4/2008 | Shores et al. | |
| 2008/0172052 A1 | 7/2008 | Eder et al. | |
| 2010/0137854 A1* | 6/2010 | Hosier | A61B 18/12 606/33 |
| 2011/0028964 A1* | 2/2011 | Edwards | A61B 18/1442 606/33 |
| 2011/0245825 A1 | 10/2011 | Mitzlaff et al. | |
| 2011/0245826 A1 | 10/2011 | Woloszko et al. | |
| 2013/0023872 A1 | 1/2013 | Mueller | |
| 2013/0150842 A1 | 6/2013 | Nau et al. | |
| 2014/0107640 A1 | 4/2014 | Yates et al. | |
| 2017/0000551 A1 | 1/2017 | Ward et al. | |

FOREIGN PATENT DOCUMENTS

| | | |
|---|---|---|
| JP | H09501328 A | 2/1997 |
| JP | 2005525861 A | 9/2005 |
| JP | 2008055167 A | 3/2008 |
| JP | 2010525867 A | 7/2010 |
| JP | 2010526557 A | 8/2010 |
| JP | 2012045405 A | 3/2012 |
| JP | 2014158705 A | 9/2014 |
| RU | 2496436 C2 | 10/2013 |
| RU | 2506903 C2 | 2/2014 |
| WO | 9426228 A1 | 11/1994 |
| WO | 0047124 A1 | 8/2000 |
| WO | 2004032777 A1 | 4/2004 |

OTHER PUBLICATIONS

First office action in corresponding Chinese Application No. 201510564810.4, dated Apr. 19, 2017, 18 pages.
Japanese office action in corresponding Japanese Application No. 2015-176612, dated Mar. 3, 2017, 4 pages.
Russian office action in corresponding Russian Application No. 2015 135 617, dated Mar. 7, 2017, 6 pages.
European Search Report for corresponding European Application No. 14183945, dated Feb. 17, 2015, 6 pages.
Office Action in corresponding Russian Application No. 2015135617/14(054548), dated Aug. 31, 2016, 9 pages.
Office Action in corresponding Japanese Application No. 2015-176612, dated Oct. 5, 2016, 5 pages.
Search Report in corresponding Japanese Application No. 2015-176612, dated Sep. 29, 2016, 48 pages.
European office action in corresponding European Application No. 14183945.6 dated Dec. 17, 2018, with English translation, 6 pages.
European Communication pursuant to Article 94(3) EPC dated Jun. 21, 2019, in corresponding European Patent Application No. 14 183 945.6, with machine English translation (8 pages).
Indian Office Action dated Oct. 26, 2020, in corresponding Indian Application No. 912/KOL/2015 (6 pages).

* cited by examiner

SYSTEM FOR SIMULTANEOUS TISSUE COAGULATION AND TISSUE DISSECTION

RELATED APPLICATIONS

This application claims the benefit of European Patent Application No. EP 14183945.6 filed Sep. 8, 2014, the contents of which are incorporated herein by reference as if fully rewritten herein.

BACKGROUND

Surgical instruments are known that can be used for cutting tissue (dissection) and for sealing tissue (coagulation).

U.S. Pat. No. 8,394,094 B2 discloses such an instrument. It is designed as a type of forceps for grasping tissue between the two branches. At one of the branches, coagulation electrodes as well as a cutting electrode are attached. The other branch serves as counter electrode. Moreover, a movable counter bearing is provided opposite to the cutting electrode.

WO 00/47124 discloses a similar instrument with a cutting electrode that is mounted movable. The cutting electrode is retained between the two sealing electrodes that are associated with counter electrodes embedded in grooves. An electric generator supplies power to this instrument from whose output voltage the coagulation voltage as well as the cutting voltage are derived. The transformer has a one-part or two part primary winding and two secondary windings. In a modified embodiment, the two output windings are connected with each other at one position. However, in any case, a voltaic separation is present between the primary winding and the secondary winding. Thereby, the core of the transformer must supply the power needed for coagulation as well as for cutting.

Experiments with various instrument configurations have shown that when the sealing and cutting occurs simultaneously, a complicated dependency between the surgical result and the technical parameters is present. The spatial configuration of the coagulation and cutting electrodes and also the type of provision of electric power or energy has a significant influence on the quality of the sealing and the incision. Both influencing factors affect the current distribution and the distribution of mechanical forces on the tissue and thus the result achieved in the biological tissue.

SUMMARY

It is the objective of the invention to provide a system that permits a safe and fast separation of tissue and sealing by means of electric energy.

The system according to the invention includes an instrument for treating biological tissue and a pertaining power supply unit. The instrument and the power supply unit are coordinated with each other in a special way. The instrument is equipped to simultaneously cut and coagulate or seal spatially distant positions of tissue. For this, a cutting electrode, a coagulation electrode or sealing electrode and a counter electrode are provided. The cutting electrode and the coagulation electrode are located at a distance to each other and preferably separated by a tissue receptacle. The branches of the instruments having the electrodes can, for example, be moved, opened and closed manually by corresponding operating levers. But the invention is not limited to such instruments; it can also be used for motor-driven branches such as, for example, in robot-controlled branches.

The power supply unit contains a transformer that has two outlets; one outlet is connected with the cutting electrode and the other is connected with the coagulation electrode. The outlets are decoupled from each other via at least one current limiting element, e.g. in the form of a coupling capacitor. The current limiting element limits the current flow to the cutting electrode and/or to the coagulation electrode so that a potentially present low tissue resistance at the cutting electrode does not impair the coagulation result and a current flow emanating from the cutting electrode does not lead to undesired coagulation manifestations. Conversely, low tissue resistance at the coagulation electrode does not impair the cutting result.

It is possible that a current limiting element is provided between the first outlet and the cutting electrode. This is viewed as being advantageous. Additionally or alternatively, a current limiting element can be provided between the second outlet and the coagulation electrode.

By means of a corresponding configuration of the current limiting elements, the treatment currents at the coagulation electrode and the cutting electrode can be adjusted independent from each other. Additionally, the coagulation result can be influenced by the voltage that is present at the outlets of the transformer. By using one or both current limiting elements, the internal resistance of the high-frequency source is adjusted as desired from the viewpoint of the respective electrode, while by means of the windings of the transformer; the no-load voltages are adjusted as desired at least at the outlet connected with the cutting electrode. As the result of the separate adjustment of voltage and current, the delivery to the cutting electrode and the sealing electrode or coagulation electrode can be optimized.

Preferably, the cross section of both branches, the first as well as the second branch is U-shaped, as a result of which a tissue receptacle is created. This tissue receptacle is located in such a way that it extends into the first as well as into the second branch. When the branches are closed, a gap can be created between them, a squeeze gap. The tissue retained in the tissue receptacle engages behind the squeeze gap and leads to a form-locked retention of the tissue in the instrument even when the cutting electrode has already cut through the retained tissue. The current limitation by the coupling capacitor or another current limiting element in combination with the design (geometry, insulation and location) of the cutting element prevents atrophy of the tissue seam while cutting.

The design of the cutting electrode in the area of its front face also influences the cutting quality. Thereby, the conducting sections in combination with the insulating regions at the front face of the cutting electrode are marked by current flow. Preferably, the cutting electrode is designed to be electrically conducting only at its small side. At its side surfaces facing the squeeze gap, it is designed electrically insulating to the largest extent. This makes a clean incision possible. Moreover, it can be achieved that the coagulation of the tissue in the receptacle is less than the coagulation of the tissue retained in the squeeze gap. In this way, tissue atrophy in the tissue receptacle is minimized and the effect of retaining the tissue during the coagulation process is maximized.

It can also be advantageous when the cutting electrode is designed partially electrically conducting at its side surfaces. Thereby, this area includes, starting at the frontal side, less than 500 µm preferably 300 µm, so that the front face projects out of the insulation with its side surfaces in this area. As the result of a cutting element that has small conducting sections at its front faces, a sufficient cutting quality can be ensured without thereby incurring too much atrophy of the tissue in the tissue receptacle.

The cutting electrode can be attached to an electrically insulating counter bearing element. This consists, for example, of plastic, for example, elastomers or ceramic. However, it is also possible to use a metallic counter bearing that is either connected with the counter electrode or is attached electrically insulated. As the result of the movability of the counter bearing element it can align corresponding to the changing thickness of the tissue retained between the counter bearing element and the cutting electrode. Preferably, the counter bearing element is mounted spring-loaded. Thus, during the cutting process it can contribute to direct the main part of the clamping forces to the squeeze gap of the coagulation electrodes and simultaneously press the atrophying tissue onto the cutting electrode, which supports the cutting process on the one hand, and on the other hand, the retention of the tissue in the squeeze gap.

The support surface of the counter bearing element can be partially or entirely flat. In particular, the shape of the counter bearing element is preferably adapted to the shape of the cutting electrode so that the cutting electrode preferably finds abutment along its entire length at the counter bearing element. The coagulation electrode can be formed by a series of individual electrodes that are located at a distance to each other. Preferably, the same applies to the counter electrode. The individual electrodes located at a distance of the coagulation electrode are preferably electrically connected with each other. Likewise, the individual electrodes of the counter electrode are preferably electrically connected with each other. But preferably, the individual electrodes of the coagulation electrode and the counter electrode are not aligned to overlap with each other so that when the branches are closed, even when no tissue is between them, no electric short circuit can occur.

Preferably, the transformer is designed in such a way that the outlet connected with the cutting electrode supplies a higher voltage than the outlet connected with the coagulation electrode. This determines the action of the cutting electrode and the counter electrode not only by the type of electrode but also by the power supply to the electrodes.

Preferably, the impedance of the current limiting element is larger than the internal resistance of the transformer at its first or at its second outlet. Thereby, the impedance refers to the high frequency that is used. Thus, the current limiting element limits (e.g. the coupling capacitor) the current so that even in the event of a short circuit at the connected electrodes, the voltage at the respectively other electrode does not collapse.

Preferably, the transformer is supplied with the coagulation voltage. Further, preferably the transformer is designed as autotransformer. Thereby, the core of the transformer must only transmit the power that is to be supplied at one of its outlets; the power supplied at the other outlet is not conveyed via the transformer core. Moreover, the number of windings is reduced as one winding is jointly used by the primary and the secondary side. This makes setting up especially space-saving and weight-saving transformers possible that can also be housed in the instrument. Alternatively, the transformer can be coupled magnetically directly with the moving coil of the generator, whereby the outlets of the transformer are connected by at least one suitable current limiting element (e.g. coupling capacitor, ohmic resistance, RC combination) with outlets of the generator.

The configuration of the power supply unit according to the invention that is described above together with the configuration of the instrument according to the invention that is described above allows the treatment of tissue, whereby the separation process of the tissue, the cutting of the tissue has ended before the sealing process of the tissue has ended and in spite of that, any bleeding of separated tissue is avoided or nearly avoided. This surprising result—that high-quality tissue separation can be performed even though the cutting process is concluded prior to the sealing process—leads to the result that the overall duration of the process of sealing tissue and cutting tissue can be reduced, which in turn leads to savings during the application. For example, the overall duration is typically three seconds shorter for the total process of cutting and sealing, of this, as a rule, less than 0.5 seconds apply to cutting the tissue. The remaining treatment time applies to the process of sealing.

For special applications it is also possible to configure the energy supply arrangement in such a way that the cutting element functions as the sealing electrode or as passive component designed without electrical function. For this, a switch can be located between the first outlet of the transformer and the cutting electrode, a potentiometer or another electrical component. The branches of the instrument are configured corresponding with the features described above. A system designed in this way makes high-quality sealing of vessels possible.

Additional details of advantageous embodiments of the invention can be learned from the drawing, the description or the dependent claims. Shown are:

BRIEF DESCRIPTION OF THE DRAWINGS

Figure 1:
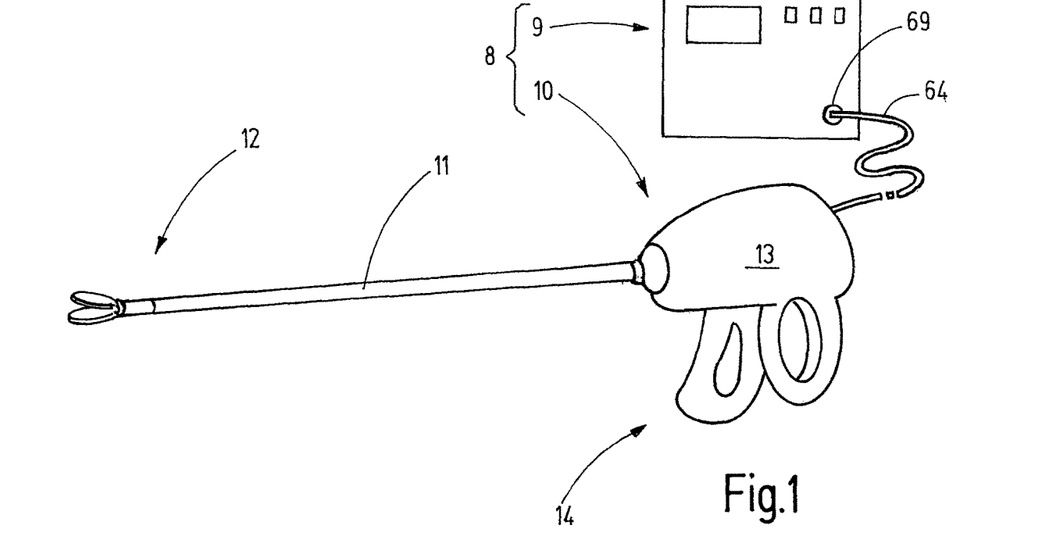
FIG. 1 shows the system in a schematized, partially perspective illustration.

FIG. 1 shows a system 8 that includes a generator 9 and a surgical instrument 10 that is supplied by such. Generator 9 feeds instrument 10 with high-frequency voltage that is conveyed to a tool 12 that is held to a shaft 11. The proximal end of shaft 11 is connected with a housing 13, at which actuation elements 14 are located to move and actuate tool 12. Tool 12 serves to cut through tissue by sealing the remaining tissue seams so that vessels contained in the tissue and lumina are sealed at the tissue seam.

Figure 2:
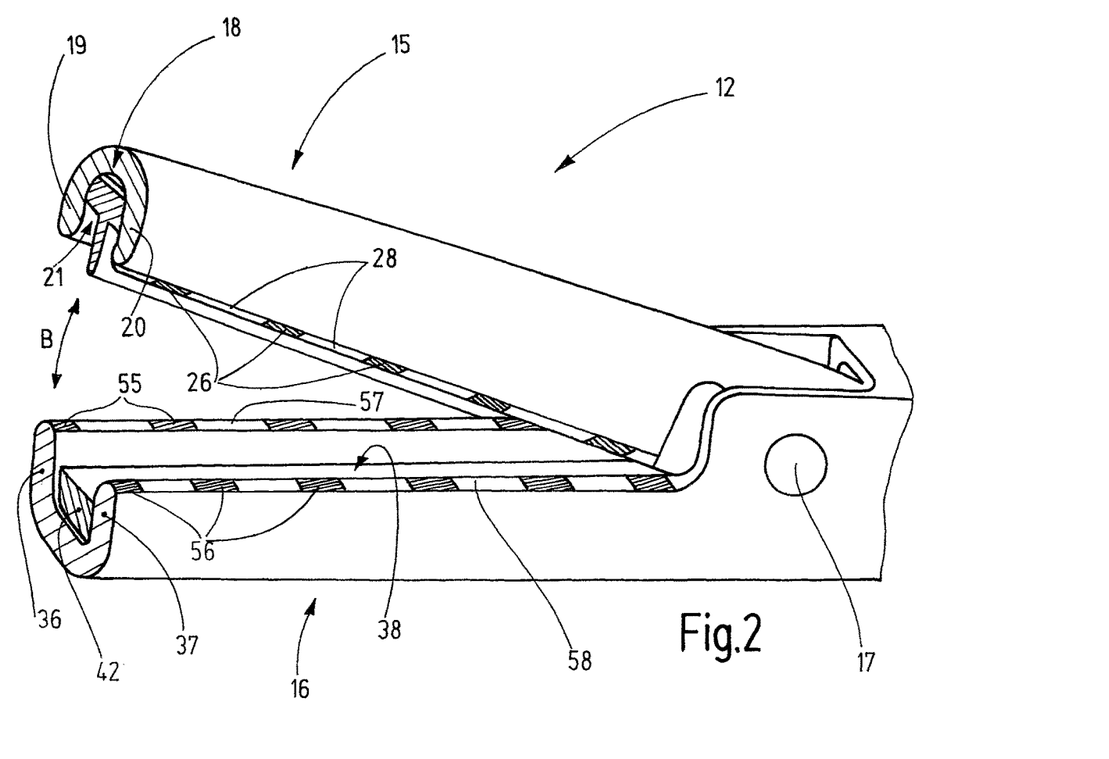
FIG. 2 shows a tool component of the instrument in the arrangement according to FIG. 1, in perspective, partially cross-sectional illustration.

The tool 12 shown in FIG. 2 has two branches 15, 16 of which at least one is mounted rotatable around a pivot axis 17. Branches 15, 16 can be moved toward each other by actuating actuation element 14, and by releasing such, away from each other. The branches 15, 16 can also be moved by other means such as, for example, pneumatic, hydraulic or electrical drives (not shown).

Figure 3:
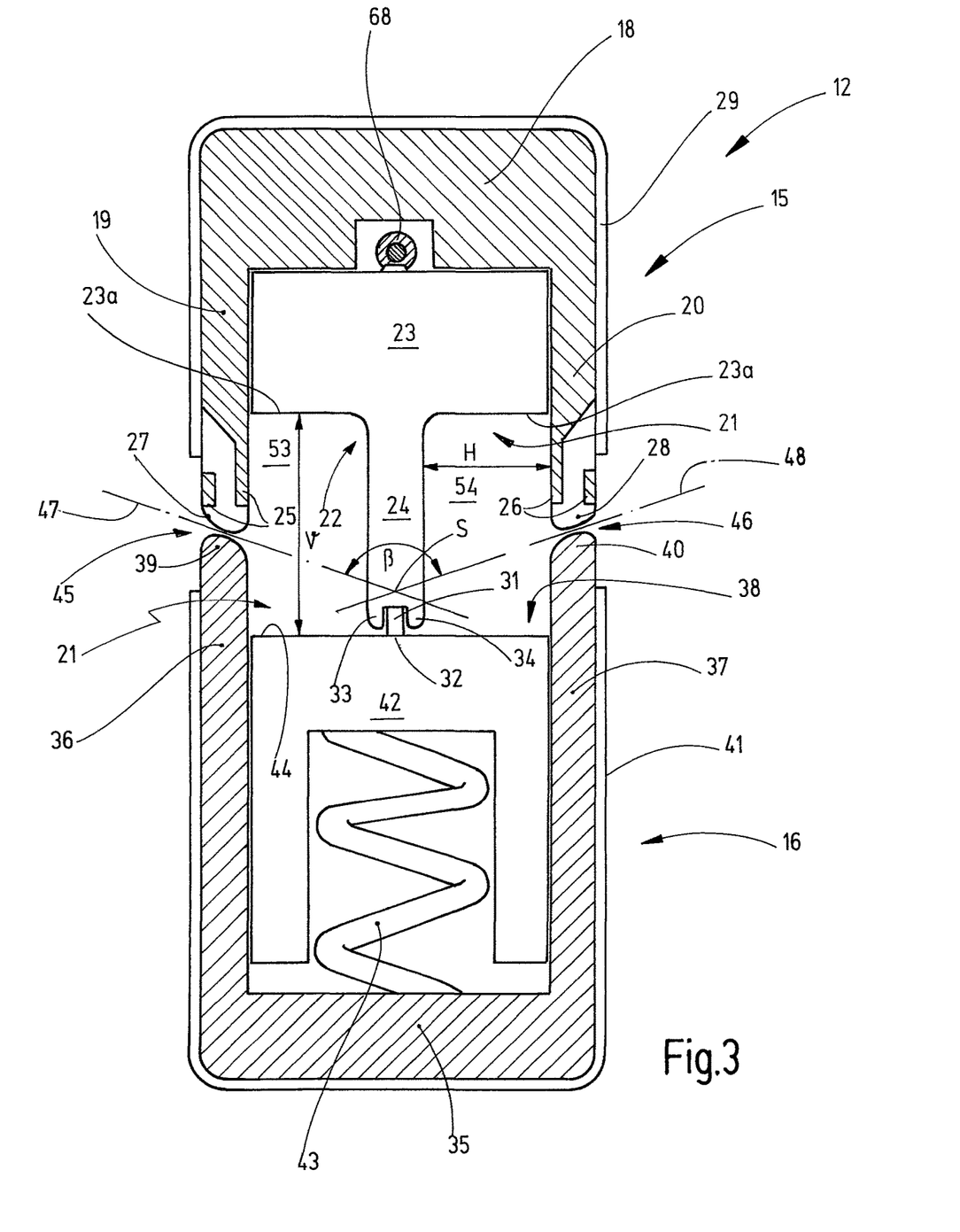
FIG. 3 shows the tool component according to FIG. 2 in vertical cross section without tissue.

The first, in FIG. 3 the upper branch 15, can consist of metal, ceramic or the like. Its main body 18 preferably has a U profile in cross section and has two parallel first sealing electrodes 19, 20 that are preferably electrically connected with each other and that delineate a space 21 between them. This space extends over a significant part of the length of the first branch 15 and serves as adapter for a cutting electrode support 22 that is preferably housed immovable with a base 23 in space 21. From the second base face 23a that is facing the second branch 16, a small, knife-like extension 24 projects that preferably projects out of space 21 that preferably ends underneath an imagined line connecting the lower ends of the sealing electrodes 19, 20.

Preferably, sealing electrode 19, 20 is designed interrupted in longitudinal direction so that it respectively has one row of single electrodes 25, 26 that can be connected electrically conducting with main body 18. The individual electrodes are separated from each other by insulating regions 27, 28. These can be applied as a type of coating to sealing electrodes 19, 20 or inserted into main body 18 as insulation bodies. Moreover, branch 15 is preferably provided with an insulating coating 29, so that main body 18 can have electrical contact only at the sealing electrodes 19, 20 but cannot have any electrical contact with biological tissue at any other positions.

On its front face, cutting electrode support 22 is provided with cutting electrode 31. Preferably, it is located in a groove or recess of the lower small side of the knife-like extension 24, whereby the cutting electrode 31 is exposed with a front face 32. Cutting electrode 31 is grasped between two groove walls 33, 34 that preferably have a width that is approximately the same size as the width of cutting electrode 31. The width of cutting electrode 31 can be in the range of 0.5 to 0.25 mm and is preferably 0.1 mm. Groove walls 33, 34 preferably have a thickness of 0.15 mm, for example. Furthermore, cutting electrode 31 can have a small protrusion over the groove walls or side walls 33, 34 that is only several micrometers, for example, 500 µm, preferably, 300 µm, particularly preferred, 200 µm, and in a special design, is preferably 0 µm to 40 µm.

Extension 24 preferably projects over coagulation electrodes 19, 20, so that an imagined line parallel to base face 23a, connecting coagulation electrodes 19, 20 preferably intersects extension 24 at approximately half its height.

The second branch 16 in FIG. 3 has a main body 35 preferably consisting of electrically conducting material that preferably has a U-shaped cross section. Its two lateral jaws 36, 37 enclose a space 38 between them and with their upper sections they form electrically conducting counter electrodes 39, 40 for sealing electrodes 19, 20 and for the cutting electrode 31.

At its outside, the main body 35 preferably has an insulating coating 41 that prevents any electrical contact with the surrounding biological tissue.

A preferably moveably mounted counter bearing 42 is located in groove 38, that is resiliently retained, movable parallel to jaws 36, 37, for example, by a spring arrangement 43 consisting of one or several springs. Counter bearing 42 is a rigid ceramic piece, for example. But it can also be designed consisting of elastic, in particular, a resilient material, for example, an elastomer. Then, it is a spring arrangement itself. The swing of the spring arrangement 43 that is designed in whatever way is thereby dimensioned in such a way that upon closing the branches and thus aligning the coagulation electrodes 19, 20 on top of the counter electrodes 39, 40 a squeeze gap 45, 46 of zero is possible and thus the maximum path of resiliency has not yet been utilized. Counter bearing 42 is in closed condition—in a preferred embodiment slightly underneath counter electrodes 39, 40.

The side of counter bearing element 42 facing cutting electrode 31 is preferably formed as a flat thrust face 44. Relative to the longitudinal direction of cutting electrode 31, thrust face 44 is preferably designed corresponding to the shape of cutting electrode 31, so that it can abut at thrust face 44 without any gap. Preferably, thrust face 44 extends between counter electrodes 39, 40 and when the branches are completely closed (without tissue) abuts at front face 32 of cutting electrode 31.

The design of thrust face 44 can be designed differently due to the selection of the material of the counter bearing 42 or due to conditions given by the application. Thus, for example, thrust face 44, when counter bearing element 42 consists of elastomers, can be designed corresponding to the shape of front face 32 of cutting electrode 31 only in the area of cutting electrode 31. Outside of this area, thrust face 44—at completely or almost completely closed branches (without tissue) can be designed raised or recessed relative to front face 32 of cutting electrode 31 (not shown).

The sealing electrodes 19, 20 and the counter electrodes 39, 40 jointly define squeeze gap 45, 46, which preferable, as lines 47, 48 in FIG. 3 indicate, are designed off-peak to counter bearing 42 so that lines 47, 48 jointly enclose an obtuse angle β and when tool 12 is closed, intersect above thrust face 44 at an intersection S.

Two tissue receptacles 53, 54 are a part of the geometry of tool 12 determining its function. These are designed on both sides of extension 24. They are limited vertically between base 23 and thrust face 44. When the branches are closed, the vertical expansion V is, for example, in the range of 0.7 mm to 2.5 mm, preferably 1.4 mm. The two tissue receptacles 53, 54 are preferably of the same size and have a horizontal expansion H that is defined by the distance between extension 24 and the respective jaw 36, 37. Preferably, the horizontal expansion H is significantly larger than the thickness of cutting electrode 31, as well as larger than the thickness of extension 24 and/or jaws 36, 37. Preferably, the horizontal expansion H is approximately 0.2 to 0.6 times as large as the vertical extension V.

The counter electrodes 39, 40 can be designed longitudinally continuous at jaws 36, 37. However, preferably they also can, as indicated in FIG. 2, consist of single electrodes 55, 56 corresponding to the design of sealing electrodes 19, 20 that are separated from each other by insulating regions 57, 58. Preferably, the insulating regions 57, 58 in the longitudinal direction of the branches are longer than the individual electrodes 55, 56. The insulating regions 57, 58 can be formed by an insulating coating or by insulation bodies. Moreover, individual electrodes 55, 56 are offset against individual electrodes 25, 26 in such a way that, that they cannot come in contact with each other even then when squeeze gap 45, 46 is zero and thus branches 15, 16 come in contact. Each individual electrode 25, 26 then meets an insulating region 57, 58. Alternatively, the structure can be designed inversely. The sealing electrodes 19, 20 and the counter electrodes 39 40 can consist of insulating material with electrically conducting individual electrodes 55, 56.

Figure 4:
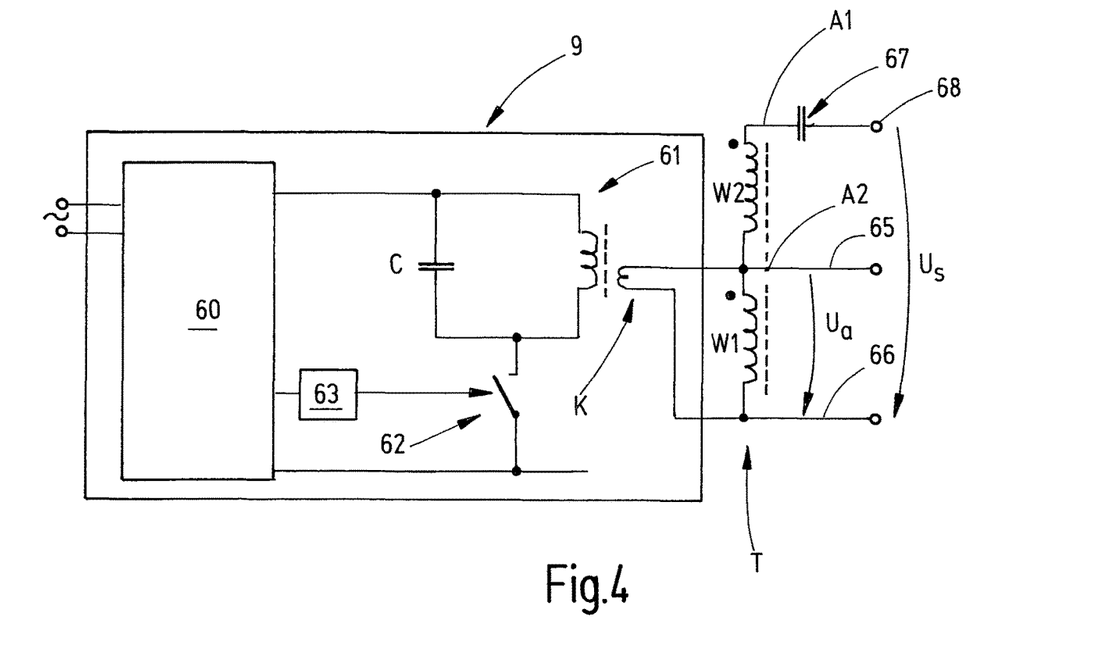
FIG. 4 shows an energy supply unit for the instrument or its tool component according to FIGS. 2 and 3 in a simplified circuit diagram.

In FIG. 4, generator 9 is shown schematically. It includes a power supply unit 60 that provides direct voltage for a high-frequency generator 61. It consists of an oscillating circuit with a capacitor C and a coil L and is excited by a controlled repeater or control element 62 depending on the specifications of a control module 63.

At coil L a coupler winding K couples out high-frequency voltage in order to deliver it via a line 64 (FIG. 1) to instrument 10. The high-frequency voltage serves the purpose of providing current to the sealing electrodes 19, 20 as well as to the cutting electrode 31. A transformer T is used to split the voltage with a primary winding W1 and at least one secondary winding W2. Preferably, transformer T is designed as an autotransformer. The primary winding W1 is connected with the outlet of high-frequency generator 61, i.e., for example, with its coupling coil (coupler winding) K.

If transformer T is an autotransformer, its inlet (i.e. the upper end of its primary winding) is simultaneously its outlet A2. From this outlet A2 and thus the outlet of high-frequency generator 61, a line 65 leads to sealing electrodes 19, 20.

A ground wire 66 that is connected with the lower end of winding W1 and coupler winding K, leads to the counter electrodes 39, 40. As a result, between the sealing electrode 19 and/or 20 and the counter electrode 39 and/or 40 the biological tissue is turned parallel to the winding W1 and is connected directly to the outlet of high-frequency generator 61. The tissue is charged with an output voltage $U_a$ for sealing.

For providing a cutting voltage $U_s$, the winding W2 is connected with its lower end with the line 65 and with its upper end with a current limiting element 67, preferably by a coupling capacitor 67 and a line 68 with the cutting electrode 31. The secondary winding W2 is poled in the same direction as the primary winding W1, co that the cutting voltage $U_s$ is the total of the output voltage $U_a$ and the voltage delivered by winding W2, whereby this total is larger than the output voltage $U_a$. Transformer T has a low leakage inductance and a low internal resistance. The coupling capacitor 67 acts current-limiting and this has the effect that the sealing electrode(s) 19, 20 are supplied with a low internal resistance and the cutting electrode 31 is supplied with an elevated internal resistance.

Figure 5:
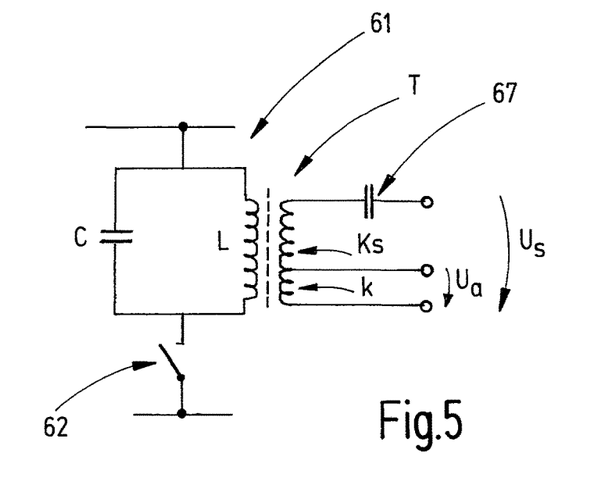
FIG. 5 shows a modified embodiment of the energy supply unit as a simplified circuit diagram.

Transformer T can be built into generator 9 or alternatively, into instrument 10. Further, alternatively, it can be provided in line 64 or at an adapter 69 that is provided on such or built into an adapter module—not shown. As FIG. 5 shows, it is also possible to combine transformer T and coil L of high-frequency generator 61. In addition to coupler winding K, a second coupler winding KS is then provided for the cutting voltage Us, which in turn delivers the high-frequency voltage outward via coupling capacitor 67.

Figure 6:
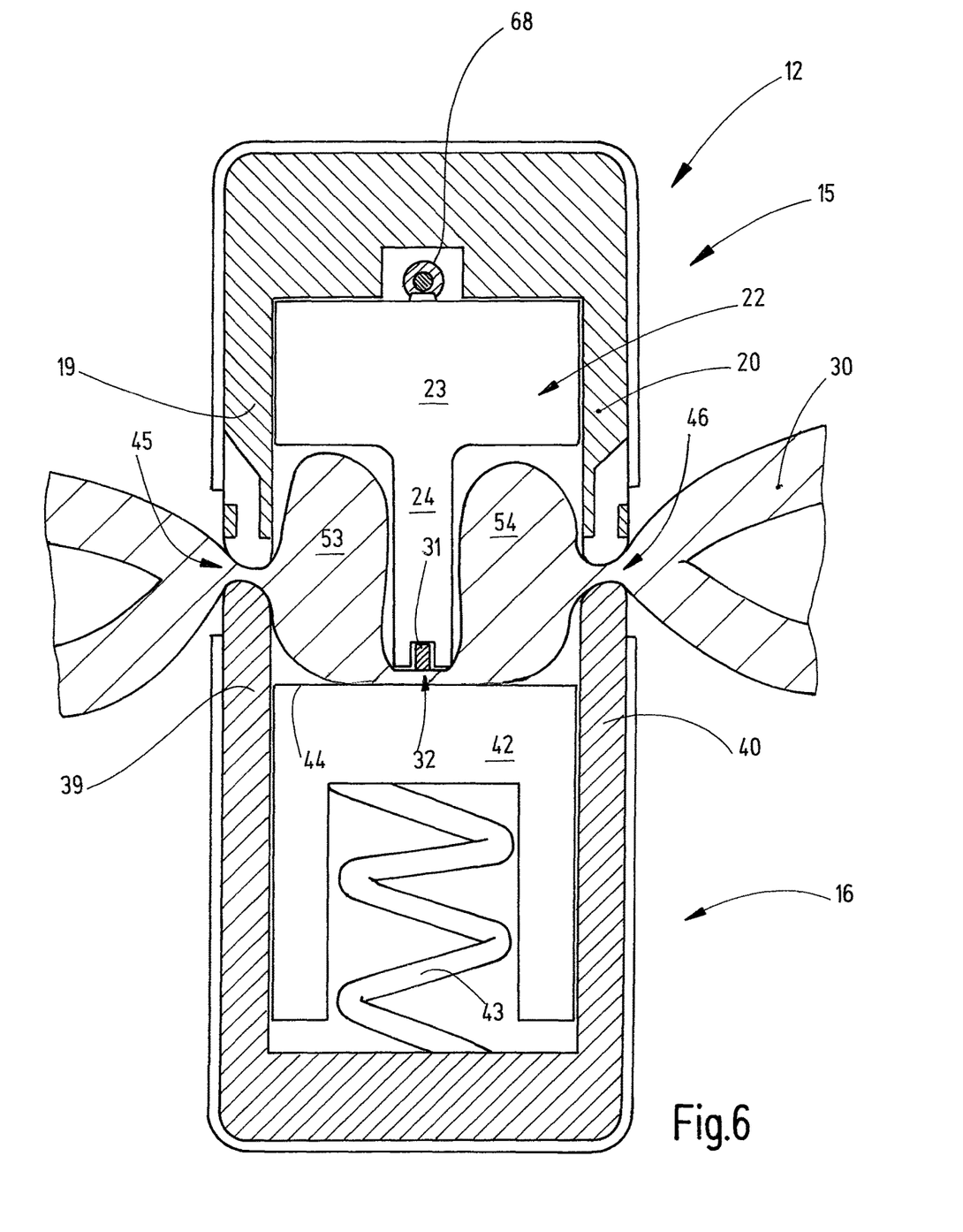
FIG. 6 shows the instrument according to FIG. 3 during coagulation and dissection of the biologic tissue in a vertically cross-sectional illustration.

Insofar, the described system 8 functions as follows:

For sealing hollow vessels, for separating body tissue, in particular, tissue containing blood vessels and which must therefore be sealed at the cutting seams, such tissue 30 as shown in FIG. 6 is grasped with tool 12 between branches 15, 16, whereby the branches are moved toward each other. As soon as the tool 12 is sufficiently closed, the high-frequency generator is actuated so that the sealing electrodes 19, 20 as well as the cutting electrode 31 are simultaneously charged with voltage relative to the counter electrodes 39, 40 and thus the tissue receives an electric charge. The tissue is pressed together in squeeze gaps 45, 46 and heated, denatured and sealed by the current passing from the sealing electrodes 19, 20 to the counter electrodes 39 40. In tissue receptacles 53, 54, the tissue atrophies to a lesser degree or not at all. The current emanating from the simultaneously charged cutting electrode 31 has a high current density at front face 32 so that the tissue is separated there by fast desiccation and by the cutting sparks produced by the high current at cutting electrode 31. However, the current density in the tissue receptacles 53, 54 is low so that almost no tissue atrophy occurs here. The tissue bulges forming there prevent that the tissue seams slide out of the tool 12 even though the tissue is cut through prior to the conclusion of the sealing process.

The cutting current is limited by the coupling capacitor 67. The cutting current is so high that after desiccation and denaturing of the tissue 45 by the cutting current at the cutting electrode 31, cutting sparks can be generated in order to produce a cut through the tissue. However, the coupling capacitor 67 is dimensioned in such a way that an increase in current to levels that would lead to high current densities in the tissue receptacles is safely precluded. Thereby, it is prevented that tissue located in tissue receptacles 53, 54 atrophies excessively and thereby escapes out of squeeze gap 45, 46 prior to the conclusion of the sealing process.

The interplay of high cutting current $U_s$ and the coupling capacitor 67 limits the cutting current during the desiccation phase of the tissue in the area of the cutting electrode and ensures, together with the tool geometry shown, the key to quick and reliable dissection of biological tissue with a high degree of cutting quality and a high degree of process safety.

Alternatively or additionally, a coupling capacitor can be provided in the line 65 for inducing current. Moreover, instead of the coupling capacitor 67, a different current limiting component or an interconnection of components can be provided that can contain one or several capacitors.

An instrument 10 provided for simultaneous coagulation and dissection of tissue has a tissue receptacle 53 between cutting electrode 31 and sealing electrode 19 for forming a tissue bulge to secure the tissue in tool 12 during the sealing process. In order to make the formation of voluminous tissue bulges possible and to prevent their atrophy, the cutting electrode 31 is supplied by a current limiting element, preferably in the form of a coupling capacitor 67. Thereby, in particular, in the case of tissue that can be cut through easily but which needs a long time to seal, a high degree of process safety can be achieved.

LIST OF REFERENCE SIGNS

| | |
|---|---|
| 8 | system |
| 9 | generator |
| 10 | instrument |
| 11 | shaft |
| 12 | tool |
| 13 | housing |
| 14 | actuation element |
| 15, 16 | branches |
| 17 | pivot axis |
| 18 | main body |
| 19, 20 | first (upper) sealing/coagulation electrodes |
| 21 | space between sealing electrodes 19, 20 |
| 22 | cutting electrode support |
| 23 | base of the cutting electrode support |
| 23a | base face |
| 24 | extension |
| 25, 26 | individual electrodes of sealing electrodes 19, 20 |
| 27, 28 | insulating regions |
| 29 | insulating coating |
| 30 | tissue |
| 31 | cutting electrode |
| 32 | front face |
| 33, 34 | groove walls |
| 35 | main body |
| 36, 37 | jaw of main body 35 |
| 38 | groove |
| 39, 40 | counter electrodes |
| 41 | insulating coating |
| 42 | counter bearing element |
| 43 | spring element |
| 44 | thrust face |
| 45, 46 | squeeze gap |
| 47, 48 | lines |
| β | obtuse angle |
| S | intersection |

-continued

| | |
|---|---|
| 53, 54 | tissue receptacles |
| V | vertical extension of the tissue receptacles 53, 54 |
| H | horizontal extension of the tissue receptacles 53, 54 |
| 55, 56 | individual electrodes |
| 57, 58 | insulating regions |
| 59 | |
| 60 | power supply unit |
| 61 | high-frequency generator |
| C | capacitor |
| L | coil |
| K | coupler winding |
| 62 | control element |
| 63 | control module |
| T | transformer |
| 64 | line |
| 65 | line |
| 66 | ground wire |
| $U_a$ | output voltage |
| 67 | current limiting element, coupling capacitor |
| $U_s$ | cutting voltage |
| 68 | line |
| 69 | adapter |
| KS | coupler winding |

What is claimed is:

1. A system (8) comprising an instrument (10), comprising:
    at least two coagulation electrodes (19, 20),
    a single cutting electrode (31),
    at least two counter electrodes (39, 40),
    an energy supply unit comprising a generator (9), a single-phase transformer (T) having only a single primary winding (W1), wherein the single primary winding is connected to an outlet of the generator, and a first outlet of the single-phase transformer (A1) that is connected with the cutting electrode (31), and a second outlet of the single-phase transformer (A2) that is connected with the coagulation electrodes (19) such that the single-phase transformer simultaneously provides a cutting voltage to the single cutting electrode and a coagulation voltage to the coagulation electrodes so that the cutting and coagulation electrodes are active at the same time to begin cutting and coagulation of tissue by the respective electrodes simultaneously, and
    at least one current limiting element (67) located between the first outlet (A1) and the single cutting electrode (31), wherein the at least one current limiting element is a capacitor configured such that the cutting electrode is supplied with an elevated internal resistance and the coagulation electrodes are supplied with a lower internal resistance than the single cutting electrode,
    wherein no switch is present between the first and second outlets of the single-phase transformer and the respective cutting and coagulation electrodes such that cutting and coagulation electrodes are each active at the same time whenever the single-phase transformer is active,
    wherein the single cutting electrode (31), the coagulation electrodes (19, 20) and the counter electrodes (39, 40) are located in branches (15, 16) of a tool (12) and arranged such that the single cutting electrode is disposed between opposing pairs of the coagulation and counter electrodes, such that one of the branches can be moved toward and away from another of the branches.

2. The system according to claim 1, wherein the single cutting electrode (31) and the counter electrodes (39, 40) are located at two different ones of the branches (15, 16) of the instrument (10), of which at least one branch (15) of the branches can be moved toward and away from another of the branches and that specify a squeeze gap (45, 46) that is separated from the cutting electrode (31) by a tissue receptacle (53, 54).

3. The system according to claim 2, wherein the tissue receptacle (53, 54) extends above the squeeze gap (45, 46) into one of the branches (15, 16) as well as below the squeeze gap (45, 46) into another of the branches (15, 16).

4. The system according to claim 1, wherein the single cutting electrode (31) has an electrically conducting front face (32) and is substantially electrically isolated on lateral surfaces of the cutting electrode (31) facing the coagulation electrodes (19, 20).

5. The system according to claim 1, further comprising an insulated counter bearing element (42) located opposite to the single cutting electrode (31).

6. The system according to claim 5, wherein the counter bearing element (42) is mounted in a displaceable manner.

7. The system according to claim 6, wherein the counter bearing element (42) is mounted or designed in a resilient manner.

8. The system according to claim 1, wherein individual ones of the coagulation electrodes (19, 20) are formed by a series of individual electrodes (25, 26) that are at a distance to each other.

9. The system according to claim 1, wherein individual ones of the counter electrodes (39, 40) are formed by a series of individual electrodes (55) and (56) that are at a distance to each other.

10. The system according to claim 1, wherein individual ones of the coagulation electrodes (19, 20) are formed by a series of individual electrodes (25, 26) and individual ones of the counter electrodes (39, 40) are formed by a series of individual electrodes (55) and (56), wherein the individual electrodes (19, 20) of the coagulation electrodes (19) and the individual electrodes (55, 56) of the corresponding counter electrodes (39, 40) are arranged so that they do not overlap each other.

11. The system according to claim 1, wherein the single-phase transformer (T) is designed such that the first outlet (A1) delivers a higher voltage than the second outlet (A2).

12. The system according to claim 1, wherein impedance of the current limiting element (67) is larger than an internal resistance of the single-phase transformer (T) at its first outlet (A1).

13. The system according to claim 1, wherein impedance of the current limiting element (67) is larger than an internal resistance of the single-phase transformer (T) at its second outlet (A2).

14. The system according to claim 1, wherein the single primary winding (W1) of the single-phase transformer (T) is supplied with a coagulation voltage (Ua), and outlet voltages provided at the first outlet (A1) and the second outlet (A2) are dimensioned such that cutting starts at a same time as a coagulation process and is finished prior to ending of the coagulation process.

15. The system according to claim 5 wherein the counter bearing element (42) is formed by an elastomer.

16. The system according to claim 1, wherein there is no capacitor electrically connected between the second outlet of the single-phase transformer and the coagulation electrodes.

17. A system (8) comprising an instrument (10), comprising:
    at least two coagulation electrodes (19, 20),
    at least one cutting electrode (31),
    at least two counter electrodes (39, 40),
    an energy supply unit comprising a generator (9), a single-phase transformer (T) having only a single primary winding (W1), wherein the single primary winding is connected to an outlet of the generator, and a first outlet of the single-phase transformer (A1) that is connected with the cutting electrode (31), and a second outlet of the single-phase transformer (A2) that is connected with the coagulation electrodes (19, 20) such that the single-phase transformer simultaneously provides a cutting voltage to the cutting electrode and a coagulation voltage to the coagulation electrodes so that the cutting and coagulation electrodes are active at the same time to begin cutting and coagulation of tissue by the respective electrodes simultaneously, and at least one current limiting element (67) located between the first outlet (A1) and the cutting electrode (31), wherein the at least one current limiting element is a capacitor, wherein an impedance of the capacitor is larger than an internal resistance of the single-phase transformer (T) at the first outlet (A1) or the second outlet (A2), wherein no switch is present between the first and second outlets of the single-phase transformer and the cutting and coagulation electrodes such that cutting and coagulation electrodes are each active at the same time whenever the single-phase transformer is active, wherein the cutting electrode (31), the coagulation electrodes (19, 20) and the counter electrodes (39, 40) are located in branches (15, 16) of a tool (12) and arranged such that the cutting electrode is disposed between opposing pairs of the coagulation and counter electrodes, such that one of the branches can be moved toward and away from another of the branches.

* * * * *